United States Patent [19]

Misra

[11] Patent Number: 4,883,809
[45] Date of Patent: Nov. 28, 1989

[54] 7-OXABICYCLOHEPTANE IMINO INTERPHENYLENEOXY SUBSTITUTED PROSTAGLANDIN ANALOGS USEFUL IN THE TREATMENT OF THROMBOTIC AND VASOSPASTIC DISEASE

[76] Inventor: Raj N. Misra, 12 Eaton Pl., Hopewell, N.J. 08525

[21] Appl. No.: 272,378

[22] Filed: Nov. 17, 1988

[51] Int. Cl.$^4$ .................. A61K 31/34; C07D 307/00
[52] U.S. Cl. ..................... 514/469; 549/463
[58] Field of Search .............. 549/463; 519/469

[56] References Cited

U.S. PATENT DOCUMENTS

| | | | |
|---|---|---|---|
| 4,416,896 | 11/1983 | Nakane et al. | 549/463 |
| 4,418,076 | 11/1983 | Nakane et al. | 549/463 |
| 4,463,015 | 7/1984 | Haslanger et al. | 549/463 |
| 4,474,804 | 10/1984 | Das et al. | 549/463 |
| 4,522,949 | 6/1985 | Das et al. | 549/463 |
| 4,536,513 | 8/1985 | Das et al. | 549/463 |

Primary Examiner—Mary C. Lee
Assistant Examiner—Barry Dentz
Attorney, Agent, or Firm—Burton Rodney

[57] ABSTRACT

7-Oxabicycloheptane imino interphenyleneoxy substituted prostaglandin analogs are provided having the structural formula

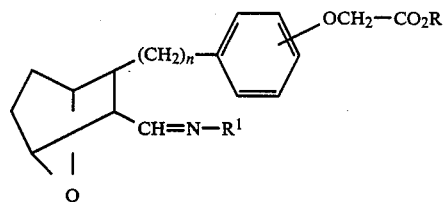

wherein
n is 1 or 2;
R is H; lower alkyl, or alkali metal; and
R$^1$ is —OR$^2$,

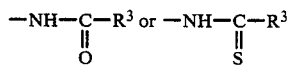

where
R$^2$ is lower alkyl, aryl, aralkyl, alkanoyl or aroyl; and
R$^3$ is lower alkyl, aryl, aralkyl, alkoxy, aryloxy, aralkoxy, —NHaralkyl, —NHalkyl or —NHaryl. The compounds are useful in the treatment of thrombotic disease.

20 Claims, No Drawings

7-OXABICYCLOHEPTANE IMINO INTERPHENYLENEOXY SUBSTITUTED PROSTAGLANDIN ANALOGS USEFUL IN THE TREATMENT OF THROMBOTIC AND VASOSPASTIC DISEASE

DESCRIPTION OF THE INVENTION

The present invention relates to 7-oxabicycloheptane substituted prostaglandin analogs which are cardiovascular agents useful, for example, in the treatment of thrombotic and/or vasospastic disease. These compounds have the structural formula

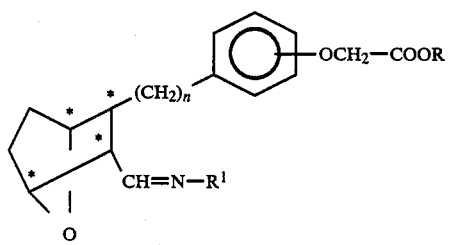

and including all stereoisomers thereof, wherein
n is 1 or 2;
R is H, alkali metal or lower alkyl; and
$R^1$ is $-OR^2$,

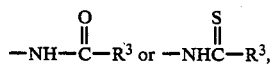

wherein
$R^2$ is lower alkyl, aryl, aralkyl, alkanoyl or aroyl, and
$R^3$ is lower alkyl, aryl, aralkyl, alkoxy, aryloxy, aralkoxy, alkylamino, arylamino or aralkylamino.

Thus, the compounds of the invention encompass the following types of compounds:

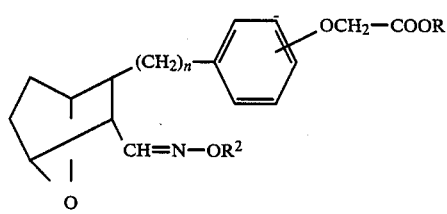

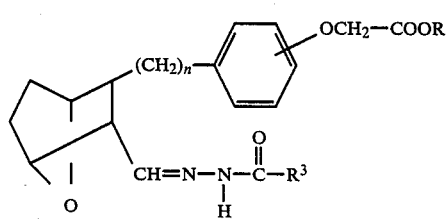

and

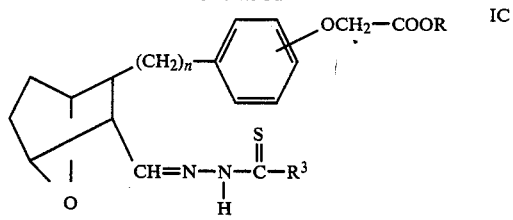

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "alkanoyl" refers to lower alkyl linked to a carbonyl (CO).

The term "aroyl" refers to aryl linked to a carbonyl (CO).

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent or either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

Preferred are those compounds of formula I wherein n is 1, R is H, $R^1$ is

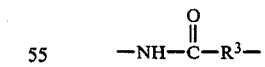

where $R^3$ is alkylamino or arylamino and the $-O-CH_2-COOR$ is in the meta or ortho position.

The various compounds of the invention may be prepared as outlined below.

Bromophenylalkyl alcohol A

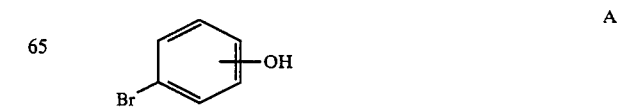

is treated with a protecting compound such as chloro-t-butyldimethylsilane or benzyl bromide, employing conventional procedures to form the protected bromophenyl compound B

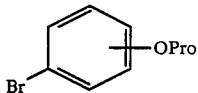

wherein Pro represents a protecting group.

Examples of protecting compounds suitable for use herein in reacting with bromophenethyl alcohol A include but are not limited to

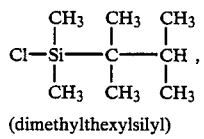
(dimethylthexylsilyl)

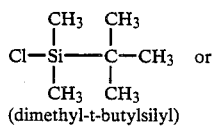
(dimethyl-t-butylsilyl)

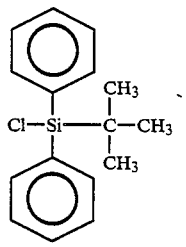
(diphenyl-t-butylsilyl), or

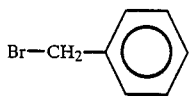

The protected compound B is then transmetallated by treatment with t-$C_4H_9Li$ in the presence of ethyl ether at reduced temperature of from about $-100°$ to about $-20°$ C. (or is subjected to a Grignard reaction by treatment with magnesium in the presence of an inert organic solvent such as tetrahydrofuran (THF) or ethyl ether) and then is condensed with an aldehyde or a hemiacetal such as (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

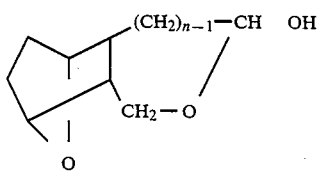

employing a molar ratio of C:B of within the range of from about 1:2 to about 1:3, in the presence of an inert organic solvent such as THF at a reduced temperature of from about $-78°$ to about $0°$ C., to form the condensed 7-oxabicycloheptane compound

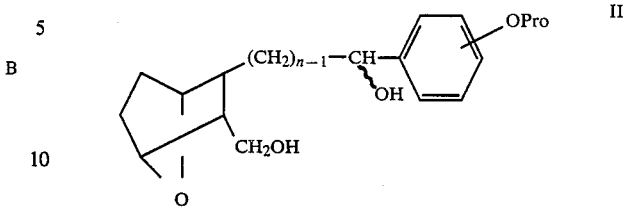

The condensed compound II is then subjected to hydrogenolysis by treatment with hydrogen in the presence of a catalyst such as palladium on charcoal in acetic acid, to form the alcohol III in the case where Pro is a silyl protecting group or to form IV directly when Pro is benzyl.

III

Compound III is deprotected by treatment with, for example, a solution of acetonitrile and aqueous hydrofluoric acid to form the deprotected alcohol IV

IV

The alcohol IV is then alkylated by treating a solution of alcohol IV in tetrahydrofuran with a molar equivalent of sodium hydride. The resulting sodium phenoxide solution is alkylated by treating with a molar equivalent of an alkylbromoacetate in the presence of an inert organic solvent such as THF or dimethylformamide, to form ester V

V

Alternatively, alcohol ester starting materials of formula V may be prepared by following the procedure as described in U.S. Pat. No. 4,536,513.

Next, the alcohol ester V is subjected to a Dess-Martin oxidation wherein a solution of alcohol ester V in methylene chloride is added to a mixture of Dess-Martin periodinane in dry methylene chloride to form the aldehyde VI

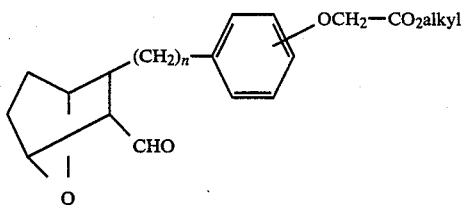

VI

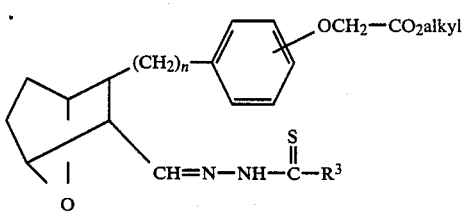

IF

The aldehyde VI is then used to prepare the imine compounds of the invention.

Compounds of the invention where $R^1$ is $-OR^2$ may be prepared by reacting aldehyde VI with an oxyamine, such as of the structure D

 D in a protic solvent such as methanol or ethanol, employing a molar ratio of aldehyde VI:D within the range of from about 0.8:1 to about 1:1 to form ester ID

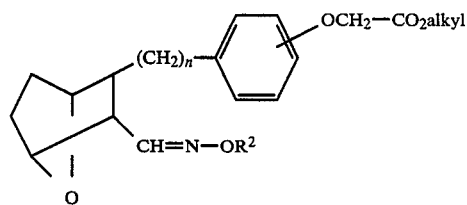

ID.

Compounds of the invention where $R^1$ is

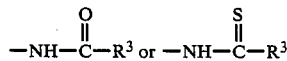

may be prepared by reacting aldehyde VI with a hydrazine derivative E or E

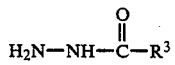 E or

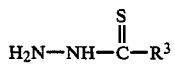 F in a protic solvent such as methanol or ethanol, to form compound IE or IF, employing a molar ratio of VI:E or F of within the range of from about 0.8:1 to about 1:1.

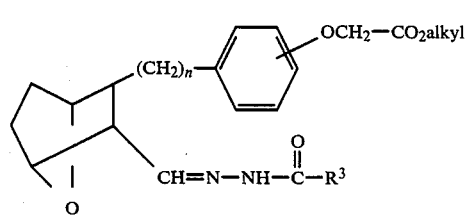

IE

The esters ID, IE and IF can be converted to the corresponding alkali metal salt (where R is Na, K or Li) by treating the esters with an alkali metal hydroxide such as NaOH, KOH or LiOH. The corresponding acid (R is H) may be formed by treating the alkali metal salts with an acid such as dilute hydrochloric acid or oxalic acid.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared by employing starting materials and following the procedures as outlined in U.S. Pat. No. 4,143,054. Examples of such stereoisomers are set out below.

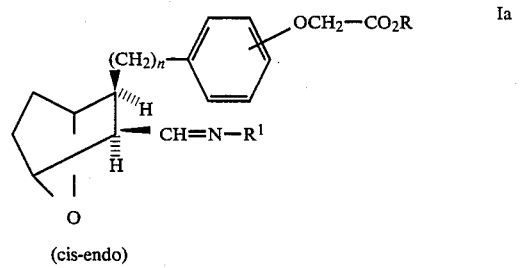

(cis-endo)

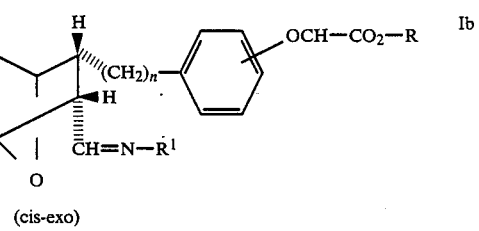

(cis-exo)

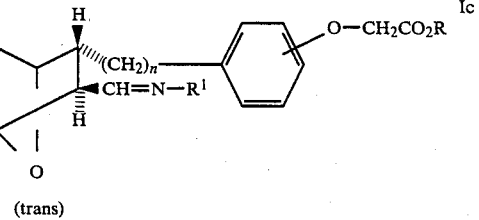

(trans)

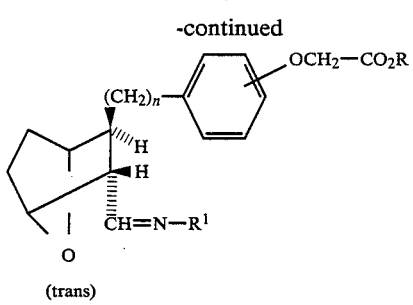

The nucleus in each of the compounds of the invention is depicted as

for matter of convenience; it will also be appreciated that the nucleus in the compounds of the invention may be depicted as

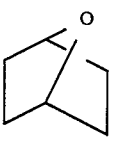

The compounds of this invention are cardiovascular agents useful as platelet aggregation inhibitors, e.g., for treatment of thrombotic disease, such as coronary or cerebral thromboses. In addition, the compounds of the invention are useful in inhibiting bronchoconstriction such as associated with asthma and airways hyperreactivity. They are also selective thromboxane $A_2$ receptor antagonists, e.g., having a vasodilatory effect for treatment of myocardial ischemic disease, such as angina pectoris.

In addition, the compounds of the invention may be useful in improving post-ischemic myocardial dysfunction, for example, decreased contractile dysfunction, decrease in tissue necrosis, and decrease in infarct size, preventing or treating toxemia in pregnancy, preventing or reducing platelet loss during extracorporeal circulation, potentiating diuretic-induced diuresis, preventing or reducing adverse reactions to protamine, preventing nephrotoxicity of drugs such as cyclosporine A, gentamycin and the like, preventing thrombosis and adverse reactions to radiographic contrast agents, preventing or reducing venous thrombosis (in conjunction with heparin), treating burn injury and promoting wound healing, treating ischemia (alone or in combination with a calcium channel blocker), preserving vascular patency and circulation during and following vascular surgery, preventing reperfusion injury after CNS ischemic states like stroke or vascular surgery, treating tardive dyskenesia, treating Raynaud's disease, treating unstable angina, treating purpura fulminarus, and treating thrombotic thrombocytopenia purpura. Furthermore, the compounds of the invention may be useful in the treatment of pulmonary embolism, diabetic retinopathy, nephritis and in coronary artery by-pass, renal dialysis, thrombolysis, endarterectomy, acute renal failure, lupus, peripheral vascular disease, intermittent claudication, pulmonary hypertension after mitral valve surgery, pulmonary hypertension after intralipid infusion, subarachnoid hemorrhage, treating or preventing complications following organ transplant (particularly cardiac or renal), treating persistent pulmonary hypertension of the newborn, treating tuberculosis and enhancing immune surveillance and promoting antibiotic penetration to sites of infection/abscess.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg (or from about 5 to about 2500 mg, preferably from about 10 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of this invention. Unless otherwise indicated, all temperatures are expressed in degrees Centigrade.

EXAMPLE 1

[1S-(1α,2β,3β,4α)]-[3-[[[(Phenylamino)carbonyl]hydrazono]methyl]-7-oxabicyclo[2.2.1]hept-2-yl]methyl]phenoxy]acetic acid ethyl ester

A. (3-Bromophenoxy) (1,1-dimethylethyl)dimethylsilane

A solution of 11.5 g (66.5 mmol, Aldrich) of m-bromophenol, 6.80 g (100 mmol, Aldrich) of imidazole and 10.3 g (68.3 mmol, Aldrich) of chloro-t-butyldimethylsilane in 75 mL of sieve-dried dimethylformamide was stirred at room temperature for 18 hours. The reaction mixture was then partitioned between 250 mL of cold 1M aqueous HCl solution and 150 mL of hexane. The organic layer was separated and the aqueous layer extracted with an additional 100 mL of hexane. The organic extracts were combined, washed with 100 mL of saturated aqueous sodium bicarbonate solution, then 100 mL of water, dried (magnesium sulfate) and concentrated in vacuo to afford 18.8 g (65.5 mmol, 99%) of title compound as a colorless oil.

B. [1S-(1α,2β,3β,4α)]-α-[3-[[(1,1-Dimethylethyl)dimethylsilyl]oxy]phenyl]-7-oxabicyclo[2.2.1]heptane-2,3-dimethanol To a solution of 18.7 g (65.1 mmol) of Part A compound in 100 mL of dry ethyl ether cooled to −78° C.

was added dropwise 46 mL (1.7M in pentane, 78 mmol, Aldrich) of t-butyllithium solution over about 30 min. The reaction mixture was stirred at −78° C. for 30 min then at 0° C. for 15 min. The resulting anion solution was re-cooled to −78° C. then added dropwise was a solution of 3.60 g (23.1 mmol) of (exo)octahydro-4,7-epoxyisobenzofuran-1-ol in 15 mL of tetrahydrofuran (THF). The reaction mixture was warmed to 0° C. and after 1 hour quenched with 5 mL of water. The resulting mixture was added to 100 mL of water, the organic phase was separated, washed with 100 mL of brine, dried (magnesium sulfate) and concentrated in vacuo to give an oil. The crude oil was purified by flash chromatography (Merck silica, 10×10 cm, 1:4 ethyl acetate/petroleum ether then ethyl acetate) to afford 7.54 g (20.7 mmol, 90%) of title compound as a colorless glass.

C.

[1S-(1α,2β,3β,4α)]-2-[[3-[[(1,1-Dimethylethyl)dimethylsilyl]oxy]phenyl]methyl]-7-oxabicyclo[2.2.1]heptane-3-methanol A mixture of 7.50 g (20.6 mmol) of Part B compound and 5.0 g of 10% palladium on carbon catalyst (Aldrich) in 100 mL of glacial acetic acid was shaken on a Parr apparatus under an atmosphere of hydrogen (40 psi) for 20 hours. TLC indicated the reaction was about ⅔ complete. The mixture was passed through a polycarbonate filter to remove the catalyst. To the filate was added 5.0 g of fresh catalyst and hydrogenation repeated as above. The resulting mixture was re-filtered to remove the catalyst and the filtrate concentrated in vacuo to give a solid. The crude material was purified by flash chromatography (Merck silica, 10×10 cm 1:1 ethyl acetate/petroleum ether) to afford 5.05 g (14.5 mmol, 70%) of title compound as a white solid, mp 106°–110° C.

D.

[1S-(1α,2β,3β,4α)]-2-[(3-Hydroxyphenyl)methyl]-7-oxabicyclo[2.2.1]heptane-3-methanol To a solution of 1.51 g (4.34 mmol) of Part C compound in 30 mL of acetonitrile was added 1.5 mL of 48% aqueous HF. The reaction mixture was stirred at room temperature for 4 hours then added to 100 mL of water and extracted with two-50 mL portions of ethyl acetate. The combined organic extracts were dried (magnesium sulfate) and concentrated in vacuo to afford 1.00 g (4.27 mmol, 98%) of title compound as a colorless oil.

E.

[1S-(1α,2β,3β,4α)]-3-[[3-(Hydroxymethyl)-7-oxabicyclo[2.2.1]hept-2-yl]methyl]phenoxy]acetic acid, ethyl ester The oil was removed from 200 mg (60% in oil, 5.0 mmol, Alfa) of sodium hydride dispersion by three washes with petroleum ether than 5 mL of dry THF was added followed by a small drop of water. To the resulting mixture was added dropwise at room temperature a solution of 980 mg (4.19 mmol) of Part D compound in 10 mL of THF. The reaction mixture was stirred for 1 hour, then 3 mL of sieve-dried (DMF) was introduced to aid in solubilizing the anion. To the resulting homogeneous solution was added 0.60 mL (5.4 mmol, Aldrich) of ethyl bromoacetate and stirred for 2 hours. The reaction mixture was added to 50 mL of 1M aqueous HCl solution and extracted with two-35 mL portions of ethyl acetate. The organic extracts were combined, dried (magnesium sulfate) and concentrated in vacuo to give an oil. The crude oil was purified by flash chromatography (Merck silica, 20×5.0 cm, 3:1 ethyl acetate/petroleum ether) to afford 695 mg (2.17 mmol, 52%) of title compound as an oil.

F.

[1S-(1α,2β,3β,4α)]-3-[[3-Formyl-7-oxabicyclo[2.2.1]hept-2-yl]methyl]phenoxy]acetic acid, ethyl ester To a mixture of 954 mg (2.25 mmol, Aldrich) of Dess-Martin periodinane in 10 mL of dry methylene chloride was added a solution of 600 mg (1.88 mmol) of Part E alcohol in 5 mL of methylene chloride. The reaction mixture was stirred for 15 minutes, then 75 mL of ethyl ether was added followed by 50 mL of saturated aqueous sodium bicarbonate solution containing 2.5 g (16 mmol) of sodium thiosulfate. The two phase mixture was stirred rapidly for 15 min. The resulting clear organic layer was separated, washed with 50 mL of saturated sodium bicarbonate solution, then 50 mL of brine, dried (magnesium sulfate) and concentrated in vacuo to give an oil. The crude material was filtered through a pad of silica gel (ether elution) and the filtrate concentrated in vacuo to afford 580 mg (1.82 mmol, 97%) of title aldehyde as a yellow oil.

G.

[1S-(1α,2β,3β,4α)]-3-[[3-[[[(Phenylamino)carbonyl]hydrazono]methyl]-7-oxabicyclo[2.2.1]hept-2-yl]methyl]phenoxy]acetic acid, ethyl ester A mixture of 340 mg (1.07 mmol) of Part F aldehyde and 178 mg (1.18 mmol, Alfa) of 4-phenylsemicarbazide in 5 mL of sieve-dried ethanol was stirred at room temperature for 16 hours. The reaction mixture was concentrated in vacuo to give a yellow oil. The crude oil was purified by flash chromatography (Merck silica, 15×3.0 cm, 2:1 ethyl acetate/petroleum ether) to afford 460 mg (1.02 mmol, 95%) of syn/anti title compound as a solid foam.

EXAMPLE 2

[1S-(1α,2β,3β,4α)]-3-[[3-[[[(Phenylamino)carbonyl]hydrazono]methyl]-7-oxabicyclo-[2.2.1]hept-2-yl]methyl]phenoxy]acetic Acid To a solution of 400 mg (0.89 mmol) of Example 1 ester in 6 mL of 2:1 THF/water was added 50 mg (1.2 mmol, Aldrich) of lithium hydroxide monohydrate. The reaction mixture was stirred rapidly for 16 hours, then acidified by addition of 1.3 mL of 1M aqueous HCl, added to 15 mL of water and extracted with two-15 mL portions of ethyl acetate. The organic extracts were combined, dried (magnesium sulfate) and concentrated in vacuo to give a solid. The solid was washed with ethyl ether then passed through a small column of silica gel (1:10:90 acetic acid/methanol/methylene chloride elution). The filtrate was concentrated in vacuo to give 225 mg (0.53 mmol, 60%) of title product, as a solid foam.

IR (KBr): 3440, 2978, 1684, 1595, 1537, 1448 cm$^1$.
270 MHz $^1$H NMR (CDCl$_3$/CD$_3$CO$_2$D):
1.40–1.90 (m, 4H)
2.40–2.70 (m, 3H)
2.80, 3.02 (dd, J=8,8, anti/syn 82:12, 1H total)
4.33, 4.37 (d, J=5, syn/anti isomers, 1H total)
4.51 (d, J=5, syn isomer, ∼0.15H)
4.61 (s overlapping with bridgehead d, —OCH$_2$—, ∼3H)

6.60 (d, J=8, syn isomer, —CH=N—, ~0.15H)
6.65–6.88 (m, 3H)
7.00–7.55 (m, 7H).

Partial 67.5 MHz $^{13}$C NMR (CDCl$_3$/CD$_3$CO$_2$D): 49.8, 50.3, 64.8, 79.7, 80.0, 112.1, 115.3, 119.8, 122.3, 123.7, 128.9, 129.6, 142.3, 146.3, 157.8.

MS(CI): 424 (M+H)+.

TLC: R$_f$(silica gel, 1:10:90 acetic acid/methanol/methylene chloride)=0.41(syn), 0.35(anti), ammonium molybdate/ceric sulfate and UV.

Analysis Calc'd for C$_{23}$H$_{25}$N$_3$O$_5$+0.25H$_2$O: C, 64.55; H, 6.01; N, 9.82. Found: C, 64.55; H, 5.97; N, 9.60.

EXAMPLE 3

[1S-(1α,2β,3β,4α)]-2-[[3-[[[(Phenylamino)carbonyl]hydrazono]methyl]-7-oxabicyclo[2.2.1]hept-2-yl]methyl]-phenoxy]acetic acid, ethyl ester

A. 1-Bromo-2-(phenylmethoxy)benzene

To a mixture of 7.45 g (43.1 mmol, Aldrich) of 2-bromophenol, and 6.9 g (50 mmol) of anhydrous potassium carbonate in 25 mL dimethylformamide (DMF) (Burdick and Jackson) heated to 80° was added dropwise 7.37 g (43.1 mmol, Aldrich) of benzyl bromide over 10 minutes. The reaction mixture was stirred at 80° for 1 hour then cooled to room temperature, added to 100 mL of water and extracted with two 50 mL portions of 1:5 ethyl ether/hexane. The organic extracts were combined, washed with 50 mL of 1M aqueous NaOH solution, 50 mL of water, dried (magnesium sulfate) and concentrated in vacuo to afford 10.6 g (40.3 mmol, 94%) of title compound as a colorless liquid.

B. [1S-(1α,2β,3β,4α)]-α-[2-(Phenylmethoxy)phenyl]-7-oxabicyclo[2.2.1]heptane-2,3-dimethanol To a solution of 8.55 g (32.5 mmol) of Part A bromide in 40 mL of dry ethyl ether (distilled from benzophenone ketyl) cooled to −78° was added dropwise 24 mL (1.7M in pentane, 41 mmol, Aldrich) of t-butyllithium. The reaction was stirred for 15 minutes then warmed to 0° for 30 minutes. The resulting solution was re-cooled to −78° and 30 mL of dry tetrahydofuran (THF) (distilled from benzophenone ketyl) was introduced followed by the dropwise addition of a solution of 1.87 g (12.0 mmol) of (exo)octahydro-4,7-epoxy-isobenzofuran-1-ol in 10 mL of THF. The reaction mixture was warmed to 0°, stirred for 2 hours then quenched with 5 mL of water. The resulting mixture was added to 150 mL of water and extracted with 100 mL of ethyl acetate. The organic layer was dried (magnesium sulfate) and concentrated in vacuo to given an oil. The crude material was purified by flash chromatography (Merck silica, 20×5 cm, 1:2 ethyl acetate/petroleum ether then 3:1 ethyl acetate/petroleum ether) to afford 1.41 g (4.15 mmol, 35%) of title compound as a colorless oil.

C. [1S-(1α,2β,3β,4α)]-2-[(2-Hydroxyphenyl)methyl]-7-oxabicyclo[2.2.1]heptane-3-methanol In a thick-walled bottle a mixture of 750 mg (2.21 mmol) of Part B compound and 1.0 g of 10% palladium on carbon catalyst in 55 mL of glacial acetic acid was shaken under an atmosphere of hydrogen (40 psi) on a Parr apparatus for 18 hours. The resulting mixture was filtered through a polycarbonate filter and the filtrate was concentrated in vacuo. The residue was partitioned between 40 mL of ethyl acetate and 40 mL of water. The organic layer was separated, washed with 40 mL of brine, dried (magnesium sulfate) and then concentrated in vacuo to afford 485 mg (2.07 mmol, 94%) of title compound as an oil.

D. [1S-(1α,2β,3β,4α)]-2-[[3-(Hydroxymethyl)-7-oxabicyclo[2.2.1]hept-2-yl]methyl]phenoxy]acetic acid, ethyl ester To a solution of 460 mg (1.96 mmol) of Part C compound in 5 mL of dry THF (distilled from Na/benzophenone) at room temperature was added in several portions a total of 85 mg (60% in oil, 2.2 mmol, Aldrich) of sodium hydride dispersion. The reaction was stirred until gas evolution ceased, about 15 minutes, then 235 μL (2.1 mmol, Aldrich) of ethyl bromoacetate was added. The reaction was mildly exothermic. The solution was stirred for 1 hour then added to 25 mL of 1M aqueous HCl solution and extracted with 25 mL of ethyl acetate. The organic extract was dried (magnesium sulfate) and concentrated in vacuo to give an oil. The crude material was purified by flash chromatography (Merck silica, 15×3 cm, 1:1 ethyl acetate/petroleum ether) to give 155 mg (0.48 mmol, 24%) of title alcohol as a colorless oil.

E. [1S-(1α,2β,3β,4α)]-2-[[3-Formyl-7-oxabicyclo[2.2.1]hept-2-yl]methyl]phenoxy]acetic acid, ethyl ester To a mixture of 235 mg (0.55 mmol, Aldrich) of Dess-Martin periodinane in 5 mL of dry methylene chloride (distilled from phosphorous pentoxide) at room temperature was added in one portion a solution of 130 mg (0.41 mmol) of Part D alcohol in 2 mL of methylene chloride. The reaction was stirred for 20 minutes then 35 mL of ethyl ether was added followed by 25 mL of saturated aqueous sodium bicarbonate solution containing 600 mg (3.8 mmol, Aldrich) of sodium thiosulfate. The two-phased mixture was stirred rapidly for 10 minutes then the resulting clear organic layer was separated, washed with 25 mL of saturated aqueous sodium bicarbonate solution, 25 mL of brine, dried (magnesium sulfate) and concentrated in vacuo to afford 122 mg (0.38 mmol, 93%) of crude title aldehyde as a colorless oil.

F. [1S-(1α,2β,3β,4α)]-2-[[3-[[[(Phenylamino)carbonyl]hydrazono]methyl]-7-oxabicyclo[2.2.1]hept-2-yl]methyl]-phenoxy]acetic acid, ethyl ester A solution of 120 mg (0.38 mmol) of Part E aldehyde and 63 mg (0.42 mmol, Alfa) of 4-phenylsemicarbazide in 3 mL of ethanol (Aldrich denaturated) was stirred at room temperature for 2 hours. The reaction mixture was concentrated in vacuo to give an oil. The crude oil was purified by flash chromatography (Merck silica, 10×3 cm, 1:1 ethyl acetate/petroleum ether) to afford 148 mg (0.33 mmol, 87%) of syn/anti title ester as a white foam.

EXAMPLE 4

[1S-(1α,2β,3β,4α)]-2-[[3-[[[(Phenylamino)carbonyl]hydrazono]methyl]-7-oxabicyclo[2.2.1]hept-2-yl]methyl]-phenoxy]acetic acid A solution of 142 mg (0.31 mmol) of Example 3 ester and 26 mg (0.62 mmol, Aldrich) of lithium hydroxide monohydrate in 6 mL of 2:1 THF/water was stirred rapidly at room temperature for 2 hours. The reaction mixture was acidified with 1 mL of 1M aqueous HCl solution then partitioned between 20 mL of water and 20 mL of ethyl acetate. The organic layer was separated, dried (magnesium sulfate) and concentrated in vacuo to afford 130 mg (0.31 mmol, 100%) of syn/anti title acid as a solid white foam.

IR(KBr): 3425 (broad), 1685, 1594, 1537, 1448, 1222 cm$^{-1}$.

Partial 67.5 MHz $^{13}$C NMR (CDCl$_3$): 173.4, 156.0, 155.9, 147.0, 137.2, 130.9, 129.0, 128.9, 127.3, 124.0, 120.4, 119.9, 119.8, 110.3, 79.7, 78.5, 63.9, 50.1, 47.9, 46.9, 32.1, 29.9.

MS (Cl): 424 (M+H)$^+$.

TLC: R$_f$(silica gel, 1:9 methanol/methylene chloride)=0.13, 0.20 (anti/syn), ammonium molybdate/ceric sulfate and UV.

Analysis Calculated for C$_{23}$H$_{25}$N$_3$O$_5$+0.25H$_2$O: C, 64.55; H, 6.00; N, 9.82. Found: C, 64.87; H, 6.21; N, 9.47.

EXAMPLE 5

[1S-(1α,2β,3β,4α)]-[3-[[3-[[[(Phenylamino)thiocarbonyl]hydrazono]methyl]-7-oxabicyclo-[2.2.1]hept-2-yl]methyl]phenoxy]acetic acid Following Example 1, Part G and Example 2, except substituting 4-phenylthiosemicarbazide for 4-phenylsemicarbazide in part G, the title acid is obtained.

EXAMPLE 6

[1S-(1α,2β,3β,4α)]-[3-[[3-[[(Pentyloxy)imino]methyl]-7-oxabicyclo[2.2.1]hept-2-yl]methyl]phenoxy]acetic acid O-Pentylhydroxyamino hydrochloride (prepared as described in Example 22 Parts A–C of U.S. Pat. No. 4,416,896) (306.9 mg, 2.2 mmol) is added to a suspension of sodium acetate (196.8 mg, 2.4 mmol) in dry ethanol (10 mL). NaCl is immediately precipitated out. Then, aldehyde prepared as described in Example 1, Part F (532 mg, 2.0 mmol) in dry ethanol (1 mL) is added at room temperature. After 1 hour stirring, the reaction mixture is poured into ethyl ether, which is washed with 1N HCl (20 mL×2) and dried over MgSO$_4$. Filtration and evaporation of solvents in vacuo give an oil which is purified by column chromatography (silica 60, 30 g) eluted with ethyl ether/petroleum ether to give the methyl ester of the title compound.

1N LiOH (6 mL) is added to the methyl ester (223 mg, 0.59 mmol) in tetrahydrofuran (30 mL) and H$_2$O (6 mL) at room temperature. After 6 hours stirring at room temperature, the reaction is quenched by addition of 1N HCl (6 mL) and poured into brine (20 mL). The products are extracted with ethyl ether (100 mL×3). The combined ether layers is washed with brine (50 mL×3) and dried over Na$_2$SO$_4$. Filtration and evaporation of solvent yield the product which is purified by a silica gel column eluted with CH$_2$Cl/CH$_3$OH to give the title product.

Examples of additional compounds in accordance with the present invention which may be prepared following the procedures outlined in the specification and working Examples and in U.S. Pat. No. 4,416,896, include, but are not limited to the following:

| Example No. | n | —OCH$_2$—CO$_2$R (position) | R$^1$ |
|---|---|---|---|
| 7 | 1 | (4) | OCH$_3$ |
| 8 | 2 | (3) | OC$_6$H$_5$ |
| 9 | 1 | (2) | OC(=O)CH$_3$ |
| 10 | 2 | (2) | OC(=O)C$_6$H$_5$ |
| 11 | 1 | (3) | —N(H)—C(=O)—C$_2$H$_5$ |
| 12 | 2 | (2) | —N(H)—C(=O)—C$_6$H$_5$ |
| 13 | 1 | (4) | —N(H)—C(=O)—OCH$_3$ |
| 14 | 2 | (4) | —N(H)—C(=O)—OC$_6$H$_5$ |
| 15 | 1 | (3) | —N(H)—C(=O)—N(H)C$_2$H$_5$ |
| 16 | 2 | (2) | —N(H)—C(=O)—N(H)—C$_6$H$_5$ |
| 17 | 1 | (2) | —N(H)—C(=S)—N(H)—C$_6$H$_5$ |
| 18 | 2 | (3) | —N(H)—C(=S)—N(H)—C$_6$H$_5$ |
| 19 | 1 | (3) | —N(H)—C(=S)—N(H)—OC$_4$H$_9$ |
| 20 | 2 | (3) | —N(H)—C(=S)—N(H)—OC$_6$H$_5$ |
| 21 | 1 | (3) | —N(H)—C(=S)—N(H)—C$_3$H$_7$ |
| 22 | 2 | (4) | —N(H)—C(=S)—N(H)—CH$_2$—C$_6$H$_5$ |
| 23 | 1 | (2) | —N(H)—C(=S)—N(H)—CH$_2$—C$_6$H$_5$ |
| 24 | 2 | (3) | —N(H)—C(=O)—N(H)—CH$_2$—C$_6$H$_5$ |

What is claimed is:
1. A compound having the formula

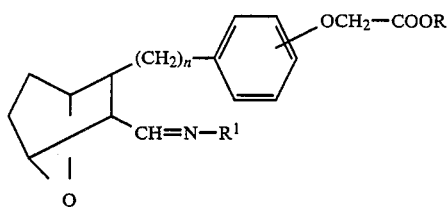

including all stereoisomers thereof, wherein
n is 1 or 2;
R is H, alkali metal or lower alkyl; and
R¹ is —OR²,

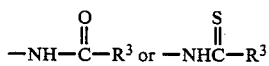

wherein
R² is lower alkyl, aryl, aralkyl, alkanoyl or aroyl; and
R³ is lower alkyl, aryl, aralkyl, alkoxy, aryloxy, aralkoxy, alkylamino, arylamino, or aralkylamino;
wherein lower alkyl or alkyl by itself or as part of another group may be unsubstituted or substituted with halo, aryl, alkyl-aryl, haloaryl, cycloalkyl or alkylcycloalkyl;
aryl by itself or as part of another group may be unsubstituted or substituted with 1 or 2 lower alkyl groups, 1 or 2 halogens and/or 1 or 2 lower alkoxy groups; and cycloalkyl by itself or as part of another group may be unsubstituted or substituted with 1 or 2 halogens, 1 or 2 lower alkyl groups and/or 1 or 2 lower alkoxy groups.

2. The compound as defined in claim 1 having the formula

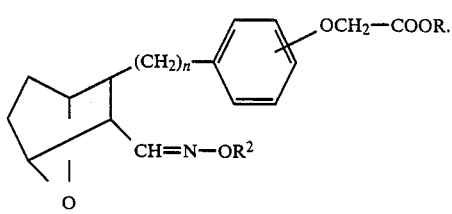

3. The compound as defined in claim 1 having the formula

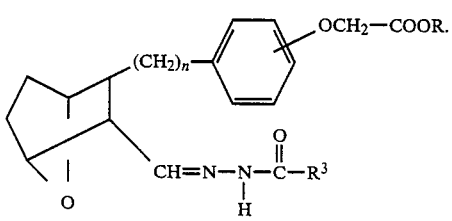

4. The compound as defined in claim 1 having the formula

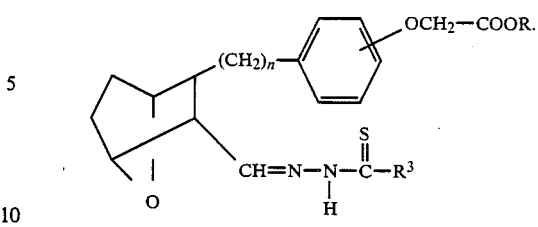

5. The compound as defined in claim 1 wherein —O—CH₂—COOR is in the meta-position or ortho-position.

6. The compound as defined in claim 3 having the formula

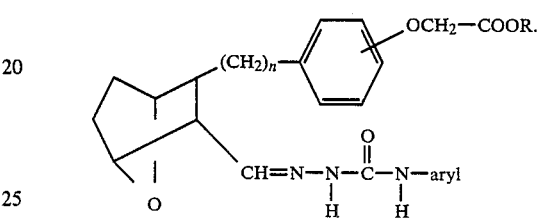

7. The compound as defined in claim 6 having the formula

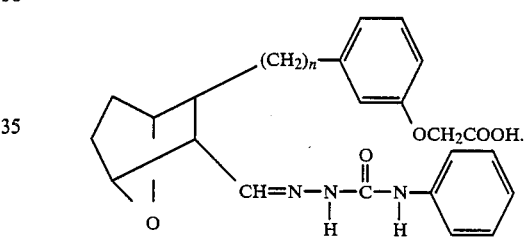

8. The compound as defined in claim 7 having the name [1S-(1α,2β,3β,4α)]-[3-[[3-[[[(phenylamino)carbonyl]hydrazono]methyl]-7-oxabicyclo[2.2.1]-hept-2-yl]methyl]phenoxy]acetic acid, or its ethyl ester.

9. The compound as defined in claim 7 having the name [1S-(1α,2β,3β,4α)]-[2-[[3-[[[(phenylamino)carbonyl]hydrazono]methyl]-7-oxabicyclo[2.2.1]-hept-2-yl]methyl]phenoxy]acetic acid, or its ethyl ester.

10. A composition for inhibiting platelet aggregation and bronchoconstriction comprising an effective amount of a compound as defined in claim 1 and a pharmaceutically acceptable carrier therefor.

11. A method of inhibiting platelet aggregation and bronchoconstriction, which comprises administering to the circulatory system of a mammalian host an effective amount of a compound as defined in claim 1.

12. The method as defined in claim 11 wherein said compound is administered in an amount within the range of from about 1 to about 100 mg/kg.

13. A method of inhibiting platelet aggregation which comprises administering to a mammalian host an effective amount of a compound as defined in claim 1.

14. A method of inhibiting bronchoconstriction associated with asthma, which comprises administering to a mammalian host an effective amount of a compound as defined in claim 1.

15. A method for improving post-ischemic myocardial dysfunction, which comprises administering to a mammalian host in need of such treatment an effective amount of a compound as defined in claim 1.

16. A method for treating toxemia during pregnancy, which comprises administering to a mammalian host in need of such treatment an effective amount of a compound as defined in claim 1.

17. A method for preventing or reducing venous thrombosis which comprises administering to a mammalian host in need of such treatment an effective amount of a compound as defined in claim 1.

18. A method for preventing or reducing platelet loss during extracorporeal circulation, which comprises administering to a mammalian host in need of such treatment an effective amount of a compound as defined in claim 1.

19. A method for treating burn injuries and/or promoting wound healing, which comprises administering to a mammalian host in need of such treatment an effective amount of a compound as defined in claim 1 in systemic or topical form.

20. A method for treating migraine headaches, which comprises administering to a mammalian host in need of such treatment an effective amount of a compound as defined in claim 1.

* * * * *